United States Patent [19]

Anderson

[11] 4,351,893

[45] Sep. 28, 1982

[54] DERIVATIVES OF ARYL KETONES AS VISIBLE SENSITIZERS OF PHOTOPOLYMERIZABLE COMPOSITIONS

[75] Inventor: Albert G. Anderson, Wilmington, Del.

[73] Assignee: E. I. Du Pont de Nemours and Company, Wilmington, Del.

[21] Appl. No.: 221,887

[22] Filed: Dec. 31, 1980

[51] Int. Cl.$^3$ .............................................. G03C 1/68
[52] U.S. Cl. .................................... 430/281; 430/910; 430/919; 430/920; 204/159.18; 204/159.23
[58] Field of Search ............... 430/919, 281, 910, 920; 204/159.18, 159.23

[56] References Cited

U.S. PATENT DOCUMENTS

| | | | |
|---|---|---|---|
| 3,257,202 | 6/1966 | Schlesinger | 96/1.5 |
| 3,617,288 | 11/1971 | Hartman et al. | 96/90 |
| 3,652,275 | 3/1972 | Baum | 204/159.14 |
| 4,162,162 | 7/1979 | Bueber | 96/115 |
| 4,268,667 | 5/1981 | Anderson | 430/919 |

Primary Examiner—Jack P. Brammer
Attorney, Agent, or Firm—James A. Costello

[57] ABSTRACT

Sensitizers for photopolymerizable compositions, the sensitizers being $\alpha,\beta$-unsaturated ketones derived from acetyltetrahydronaphthalene or acetylindane and dialkylaminoaryl aldehyde; and the photopolymerizable compositions comprising said sensitizers.

9 Claims, No Drawings

DERIVATIVES OF ARYL KETONES AS VISIBLE SENSITIZERS OF PHOTOPOLYMERIZABLE COMPOSITIONS

BACKGROUND OF THE INVENTION

1. Field Of The Invention

Sensitizers comprising $\alpha,\beta$-unsaturated ketones derived from acetyltetrahydronaphthalene or acetylindane and dialkylaminoaryl aldehydes; and photopolymerizable compositions comprising said sensitizers.

2. Description Of The Prior Art

Use of sensitizers to extend the photosensitivity of photopolymerizable compositions into the visible region of the spectrum and to increase the speed of polymerization is known. Baum et al, U.S. Pat. No. 3,652,275, disclose selected bis(p-dialkylaminobenzylidene) ketones as sensitizers to enhance the efficiency of hexaarylbiimidazole initiator systems in photopolymerizable compositions.

Dueber, U.S. Pat. No. 4,162,162, discloses photopolymerizable compositions comprising a photopolymerizable monomer, a hexaarylbiimidazole initiator, and a sensitizing amount of a compound derived from aryl ketones and p-dialkylaminoaryl aldehydes. Alkyl-substituted 1-phenyl-2-propen-1-ones are disclosed, and a methylenedioxy heterocyclic-substituted 1-phenyl-2-propen-1-one is exemplified (Example 21). There is no disclosure of a carbocyclic-substituted 1-phenyl-2-propen-1-one.

Hartman et al, U.S. Pat. No. 3,617,288, disclose the use of substituted 2-propen-1-ones as sensitizers for photolyzable organic halogen compounds. The sensitizers are free of amine groups more basic than the diphenylamino radical.

Schlesinger et al, U.S. Pat. No. 3,257,202, disclose polymerization products of olefinic ketones as photoconductor coatings for electrophotographic purposes. Certain 1-phenyl-2-propen-1-ones are disclosed, but there is no disclosure of a carbocyclic-substituted 1-phenyl-2-propen-1-one.

SUMMARY OF THE INVENTION

The ketone sensitizers of this invention have the formula

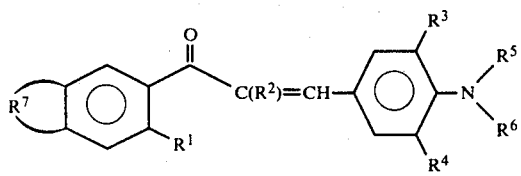

wherein:
- $R^1$ and $R^2$ are each H, or $R^1+R^2$ is $-CH_2-$;
- $R^3$ is H, or $R^3+R^5$ is selected from $-(CH_2)_2-$, $-(CH_2)_3-$, and $-CH(CH_3)CH_2C(CH_3)_2-$;
- $R^4$ is H, or $R^4+R^6$ is selected from $-(CH_2)_2-$ and $-(CH_2)_3-$;
- $R^5$ and $R^6$ are alkyl groups of 1 to 5 carbon atoms, or together are selected from $-(CH_2)_4-$ and $-CH_2CH_2OCH_2CH_2-$;
- $R^7$, having a total of up to 8 carbon atoms, is selected from trimethylene and tetramethylene groups, unsubstituted, or substituted with 1 to 4 alkyl groups.

Preferred sensitizers are those wherein $R^1$ and $R^2$ are H, and $R^7$ is unsubstituted. Most preferred are sensitizer compositions where $R^5$ and $R^6$ are each $CH_3$ or $C_2H_5$, or $R^3+R^5$ is $-(CH_2)_3-$. Preference is based on ease of preparation and sensitizer performance.

The invention also concerns photopolymerizable compositions containing the sensitizers of Formula I. The photopolymerizable compositions of this invention comprise a combination of:

(i) at least one nongaseous ethylenically unsaturated compound capable of forming a high molecular weight polymer by photoinitiated addition polymerization;

(ii) at least one 2,4,5-triarylimidazolyl dimer initiator consisting of two 2,4,5-triarylimidazolyl radicals bound together by a single covalent bond; and (iii) at least one $\alpha,\beta$-unsaturated ketone sensitizer of formula I.

For practical considerations, it is preferred to employ a compound (i) which has a boiling point above 100° C. at normal atmospheric pressure.

The photopolymerizable compositions can contain a polymeric binder to improve strength or to improve or effect adherence to a substrate. The relative concentrations of elements (i), (ii), and (iii), and the binder are as follows. The ethylenically unsaturated compound, (i), is present in an amount of about 3 to 100 parts per 100 parts of the combined weight of (i) and binder; the binder being present in an amount of 0 to about 97 parts per 100 parts of their combined weight. The initiator, (ii), is present in an amount of about 0.01 to 20 parts per 100 parts of the combined weight of (i) and binder. The sensitizer, (iii), is present in an amount of about 0.001 to 15 parts per 100 parts of the combined weight of (i) and binder, more preferably at about 1.0 to 10 parts per 100 parts.

The photopolymerizable compositions of this invention can contain other additives in addition to binders. The types and amounts of such additives will be obvious to those skilled in the art. Several types of additives will be described hereafter.

DETAILS OF THE INVENTION

Preparation of Sensitizers

The sensitizers of this invention are prepared by condensing the appropriate acetyltetrahydronaphthalene, acetylindane, or corresponding cyclic carbonyl compound, with a p-dialkylaminobenzaldehyde in the presence of a base such as sodium hydroxide, to give the $\alpha,\beta$-unsaturated ketones of the invention. Ketone starting materials wherein $R^1=R^2=H$ are generally prepared by reaction of the corresponding hydrocarbons, e.g., tetrahydronaphthalene or indane, with acetyl chloride or acetic anhydride in the presence of aluminum chloride to obtain the desired acetyl derivatives. Cyclic ketones wherein $R^1+R^2$ is $-CH_2-$ can be prepared by reaction of the corresponding hydrocarbon, e.g., tetrahydronaphthalene or indane, with $\beta$-chloropropionyl chloride in the presence of aluminum chloride to give a $\beta$-chloropropionyl derivative followed by cyclization of this intermediate with concentrated sulfuric acid to give the desired cyclic carbonyl compound.

Photopolymerizable Compositions

The Ethylenically Unsaturated Compound (i)

Contemplated monomers include those which form both water-soluble and water-insoluble polymers. Typical monomers are alkylene or polyalkylene glycol diacrylate prepared from an alkylene glycol of 2 to 15 carbons or a polyalkylene ether glycol of 1 to 10 ether linkages, and those disclosed in Martin and Barney, U.S. Pat. No. 2,927,022, e.g., those having a plurality of addition polymerizable ethylenic linkages, particularly when present as terminal linkages, and especially those wherein at least one and preferably most of such linkages are conjugated with a doubly bonded carbon, including carbon doubly bonded to carbon and to such hetero atoms as nitrogen, oxygen and sulfur. Outstanding are such materials wherein the ethylenically unsaturated groups, especially the vinylidene groups, are conjugated with ester or amide structures.

The following specific compounds are illustrative of this class: unsaturated esters of alcohols, preferably polyols and particularly such of the alphamethylene carboxylic acids, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol trimethacrylate, 1,4-cyclohexanediol diacrylate, 1,4-benzenediol dimethacrylate, pentaerythritol tetramethacrylate, 1,3-propanediol diacrylate, 1,3-pentanediol dimethacrylate, the bisacrylates and methacrylates of polyethylene glycols of molecular weight 200–500, and the like; unsaturated amides, particularly those of the alpha-methylene carboxylic acids, and especially those of alpha-omegadiamines and oxygen-interrupted omega-diamines, such as methylene bis-acrylamide, methylene bis-methacrylamide, ethylene bis-methacrylamide, 1,6-hexamethylene bisacrylamide, diethylene triamine tris-methacrylamide, bis(gamma-methacrylamidopropoxy)ethane-beta-methacrylamidoethyl methacrylate, N-(beta-hydroxyethyl)-beta-(methacrylamido)ethyl acrylate and N,N-bis(betamethacryloxyethyl)acrylamide; vinyl esters such as divinyl succinate, divinyl adipate, divinyl phthalate, divinyl terephthalate, divinyl benzene-1,3-disulfonate, and divinyl butane-1,4-disulfonate, styrene and derivatives thereof and unsaturated aldehydes, such as sorbaldehyde (hexadienal).

An outstanding class of these preferred addition polymerizable components are the esters and amides of alpha-methylene carboxylic acids and substituted carboxylic acids with polyols and polyamines wherein the molecular chain between the hydroxyls and amino groups is solely carbon or oxygen-interrupted carbon. The preferred monomeric compounds are polyfunctional, but monofunctional monomers can also be used. In addition, the polymerizable, ethylenically unsaturated polymers of Burg U.S. Pat. Nos. 3,043,805, Martin 2,929,710 and similar materials may be used alone or mixed with other materials. Acrylic and methacrylic esters of polyhydroxy compounds such as pentaerythritol and trimethylolpropane, and acrylic and methacrylic esters of adducts of ethylene oxide and polyhydroxy compounds such as those described in Cohen and Schoenthaler, U.S. Pat. No. 3,380,831 are also useful. The photocrosslinkable polymers disclosed in Schoenthaler, U.S. Pat. Nos. 3,418,295, and Celeste, 3,448,089, may also be used. The amount of monomer added varies with the particular polymer used. Other useful ethylenically unsaturated compounds are the ethylenically unsaturated diester polyhydroxy polyethers described in U.S. Pat. Nos. 3,661,576, 3,373,075 and 3,637,618.

Many ethylenically unsaturated monomers are subject to thermal polymerization, especially when stored for long periods or at elevated temperatures. When such compounds are supplied commercially, it is customary for them to contain a small amount of a thermal polymerization inhibitor. These inhibitors can be left in the monomers when the photopolymerizable compositions of this invention are prepared, as was done in the Examples which follow. The resulting compositions usually have satisfactory thermal stability. If unusual thermal exposure is anticipated, or if monomers containing little or no thermal polymerization inhibitor are employed, compositions with adequate shelf life can be obtained by incorporating about 1 to 500 ppm by weight of monomer, of a thermal polymerization inhibitor such as hydroquinone, methylhydroquinone, p-methoxyphenol, and the nitroso dimer inhibitor systems described in Pazos, U.S. Pat. No. 4,168,982.

The Initiator (ii)

Dimers consisting of two 2,4,5-triarylimidazolyl radicals bound together by a single covalent bond are photodissociable to the corresponding triarylimidazolyl radicals. The dimers absorb maximally in the 255 to 275 nm region, and usually show some lesser absorption in the 300 to 375 nm region. Although the absorption bands tend to tail out to include wavelengths as high as about 430 nm, they normally require radiation rich in the 255 to 375 nm region for their dissociation.

Suitable 2,4,5-triarylimidazolyl dimers include 2-(o-chlorophenyl)-4,5-diphenylimidazolyl dimer, 2-(o-chlorophenyl)-4,5-di(m-methoxyphenyl)imidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2,4-di(p-methoxyphenyl)-5-phenylimidazolyl dimer, 2-(2,4-dimethoxyphenyl)-4,5-diphenylimidazolyl dimer, 2-(p-methylmercaptophenyl)-4,5-diphenylimidazolyl dimer, and the like. Other suitable dimers are disclosed by Baum and Henry in U.S. Pat. No. 3,652,275, column 5, line 44, to column 7, line 16, the disclosure of which is incorporated herein by reference.

The imidazolyl dimers can be used with a free-radical producing hydrogen or electron donor such as 2-mercaptobenzoxazole, 2-mercaptobenzthiazole, Leuco Crystal Violet or tris(4-diethylamino-2-methylphenyl)methane. Other leuco dyes, e.g., those disclosed in U.S. Pat. No. 3,652,275, column 7, line 24, to column 11, line 32, can also be used. By the term "leuco dye" is meant the colorless, i.e., reduced, form of a dye compound which can be oxidized to its colored form by the triarylimidazolyl radical.

The Sensitizer (iii)

The $\alpha,\beta$-unsaturated ketone sensitizers of this invention, described broadly above, have been found to absorb radiation in the broad spectral range of about 300 to 700 nm. The maximum absorption ($\lambda_{max}$) is in the range of about 350 to 550 nm and preferably about 400 to 500 nm.

Other Additives

It is preferred that the photopolymerizable compositions contain a polymeric binder which can serve to strengthen the composition or adhere it to a substrate. Radiation-transparent and film-forming polymer binders are preferred. Examples of suitable binders are thermoplastic macromolecular organic polymers which have number average molecular weights of at least about 1500, preferably at least about 4000, including such polymer types as: (a) copolyesters based on terephthalic, isophthalic, sebacic, adipic and hexahydroterephthalic acids; (b) nylons or polyamides; (c) vinylidene chloride copolymers; (d) ethylene/vinyl acetate copolymers; (e) cellulosic ethers; (f) synthetic rubbers; (g) cellulose esters; (h) polyvinyl esters including polyvinyl acetate/acrylate and polyvinyl acetate/methacrylate copolymers; (i) polyacrylate and α-alkylpolyacrylate esters, e.g., polymethyl methacrylate, polyethyl methacrylate, and methyl methacrylate/ethyl acrylate copolymers; (j) high molecular weight polyethylene oxides of polyglycols having average molecular weights of about 4000 to 1,000,000; (k) polyvinyl chloride and copolymers; (l) polyvinyl acetal; (m) polyurethanes; (n) polycarbonates; (o) polystyrenes.

In a particularly preferred embodiment of the invention, the polymeric binder is selected so that the unexposed photopolymerizable coating is soluble in predominantly aqueous solution, for example dilute aqueous alkaline solution, but upon exposure to actinic radiation becomes relatively insoluble therein. Typically, polymers which satisfy these requirements are carboxylated polymers such as vinyl addition polymers containing free carboxylic acid groups. A most preferred group of binders includes polyacrylate esters and poly-α-alkylacrylate esters which contain carboxyl groups; particularly preferred are the polymethyl methacrylate esters.

In preferred positive-working photopolymerizable compositions, nitroaromatic photoinhibitors as disclosed in U.S. Pat. No. 4,198,242 are present. These compounds are used in amounts of about 0.5 to 15 parts by weight per 100 parts of the combined weight of ethylenically unsaturated compound and binder.

A wide range of nonpolymerizable plasticizers are effective in achieving improved exposure and development temperature latitude. When a macromolecular binder is present in the layer, plasticizer would be selected which is compatible with the binder as well as the ethylenically unsaturated monomer and other components of the composition. With acrylic binders, for example, plasticizers can include dibutyl phthalate and other esters of aromatic acids; esters of aliphatic polyacids such as diisooctyl adipate, and nitrate esters; aromatic or aliphatic acid esters of glycols, polyoxyalkylene glycols, aliphatic polyols; alkyl and aryl phosphates; low molecular weight polyesters of poly-α-methylstyrenes; chlorinated paraffins; and sulfonamide types can be used. In general, water insoluble plasticizers are preferred for greater high humidity storage stability, but are not necessary to get improved latitude. Other inert additives can be employed such as dyes, pigments and fillers. These additives are generally present in minor amounts so as not to interfere with the exposure of the photopolymerizable layer.

Substrates For The Photopolymerizable Compositions

The photopolymerizable compositions can be coated on a wide variety of substrates. By "substrate" is meant any natural or synthetic support, preferably one which is capable of existing in a flexible or rigid film or sheet form. For example, the substrate can be a metal sheet or foil, a sheet or film of synthetic organic resin, cellulose paper, fiberboard, and the like, or a composite of two or more of these materials.

The particular substrate will generally be determined by the use application involved. For example, when printed circuits are produced, the substrate may be a plate which is a copper coating on fiberboard; in the preparation of lithographic printing plates, the substrate is anodized aluminum. Specific substrates include alumina-blasted aluminum, anodized aluminum, alumina-blasted polyethylene terephthalate film, polyethylene terephthalate film, e.g., resinsubbed polyethylene terephthalate film, polyvinyl alcohol-coated paper, crosslinked polyester-coated paper, nylon, glass, cellulose acetate film, heavy paper such as lithographic paper, and the like.

An antihalation material can be used beneath the photopolymerizable layer, for example, in the substrate or on its surface. When an antihalation layer is used between the photopolymerizable layer and the substrate, the layer must have adequate adhesion to the substrate and the photopolymerizable layer and not react with the radiation-adsorptive material. Anti-halation pigments and resin carriers are described in British Pat. No. 1,366,769.

The photopolymerizable composition is usually applied to the substrate as a solution or dispersion in a carrier solvent. The solution or dispersion can be sprayed, brushed, applied by a roller or an immersion coater, flowed over the surface, picked up by immersion or applied to the substrate by other suitable means. The solvent is then allowed to evaporate. In general, solvents are employed which are volatile at ordinary pressures. Examples of suitable solvents include water; amides such as N,N-dimethylformamide and N,N-dimethylacetamide; alcohols and ether alcohols such as methanol, ethanol, 1-propanol, 2-propanol, butanol, ethylene glycol, 2-butoxyethanol, and 2-ethoxyethanol; esters such as methyl acetate and ethyl acetate; aromatic hydrocarbons and aromatic halocarbons such as benzene, o-dichlorobenzene and toluene; ketones such as acetone, 2-butanone, and 3-pentanone; aliphatic halocarbons such as 1,1,1-trichloroethane, methylene chloride, chloroform, 1,1,2-trichloroethane, 1,1,2,2-tetrachloroethane, 1,1,2-trichloroethylene; miscellaneous solvents such as dimethyl sulfoxide, pyridine, tetrahydrofuran, 1,2-dimethoxyethane, dioxane, dicyanocyclobutane, N-methylpyrrolidone; and mixtures of these solvents in various proportions as may be required to attain solutions. Alternatively, the photopolymerizable composition can be formed into a film and the film can be applied to the substrate.

Preferably the layers of the photopolymerizable compositions have a thickness ranging from about 0.0001 inch (~2.5 μm) to 0.01 inch (~250 μm) and are applied to a thin, flexible, polymeric film support which can transmit actinic radiation to the photopolymerizable layer. The opposite side of the photopolymerizable layer can have adhered thereto a protective cover layer or cover sheet wherein the sheet has less adhesion to the layer than to the film support. A particularly preferred support is a transparent polyethylene terephthalate film having a thickness of about 0.001 inch (~25 μm). Polyethylene, 0.001 inch (~25 μm) is a preferred cover sheet; polyvinyl alcohol coating is a preferred cover layer.

Any convenient source of actinic radiation providing wavelengths in the region of the spectrum that overlap the α,β-unsaturated ketone sensitizers absorption bands can be used to activate the photopolymerizable compositions for triarylimidazolyl radical formation, image formation and photopolymerization initiation. The radiation can be natural or artificial, monochromatic or polychromatic, incoherent or coherent, and for high efficiency should correspond closely in wavelengths to the sensitizer's principal absorption bands and should be sufficiently intense to activate a substantial proportion of the sensitizer.

Conventional radiation sources include fluorescent lamps, mercury, metal additive and arc lamps providing narrow or broad radiation bands centered near 405, 436 and 546 nm (Hg) wavelengths. Coherent radiation sources are the pulsed xenon, argon ion and/or ionized neon-lasers whose emulsions fall within or overlap the visible absorption bands of the sensitizer. Ultraviolet and visible emitting cathode ray tubes widely useful in printout systems for writing on photosensitive materials are also useful with the subject compositions. These cathode ray tubes comprise an ultraviolet or visible-emitting phosphor internal coating as the means for converting electrical energy to light energy and a fiber optic face plate as the means for directing the radiation to the photosensitive target. Electron accelerators and electron beam sources through an appropriate mask are also suitable.

The radiation exposure times can vary from fractions of a second to minutes, depending upon the intensity and spectral energy distribution of the radiation used, its distance from the photopolymerizable layer, and the nature and amounts of the unsaturated compounds in the layer. Customarily, a distance of about 1.5 to 60 inches (3.8 to 153 cm) from the photopolymerizable layer is used. Exposure temperatures are not particularly critical, but it is preferred to operate at about ambient temperatures or slightly higher, i.e., about 20° to 50° C.

Imagewise exposure is conveniently carried out by exposing the photopolymizable element to actinic radiation through a process transparency, that is, an image-bearing transparency consisting of areas substantially opaque and substantially transparent to the radiation being used, where the opaque areas can be substantially of the same optical density; for example, a so-called line or halftone negative or positive. Suitable process transparencies also include those with a graded range of opaque areas; for example, a continuous tone negative. Process transparencies can be constructed of any suitable materials including cellulose acetate film and polyester film.

After exposure, the image is developed. Development can be by toning, i.e., dusting with a fine pigment which selectively adheres to the tacky unhardened areas, by dye imbibition or by modulation of diffusion. Generally, however, the portions of the layer corresponding to the unexposed portions are removed, e.g., in lithographic applications. This method of development can be achieved by pressure transfer, differential adhesion of the exposed versus unexposed areas, use of peel apart transfer, and, preferably, by solvent washout. The solvent liquid use for development should have good solvent action on the nonpolymerized portions of the composition, and little action on the insolubilized image in the time required to remove the soluble portions.

Utility

The photopolymerizable compositions of this invention have very little residual color and good solubility and shelf life. They are useful in printing plates for offset and letter press, engineering drafting films, as well as photoresists in making printed circuits or in chemical milling, and as solder masks. They are also useful in the preparation of video disks. In printing plate applications, an important use is in a positive/negative two-exposure imaging system of a positive photopolymer litho printing plate. The compositions are also useful in positive working photopolymer litho films. Still other uses are for preparing colored images from color separation negatives suitable for color-proofing. The images formed with these elements can be used for making copies by thermal transfer to a substrate. Other specific uses will be evident to those skilled in the art.

In photoresist applications, thin film resists prepared from the composition are useful in the preparation of microcircuits. The resists can be either solvent soluble or aqueous developable. Solder masks are protective coatings which are selectively applied to portions of a printed circuit board surface to confine solder to pad areas on the board and to prevent bridging between conductors during tinning operations and during soldering of components. A solder mask also functions to prevent or minimize corrosion of the base copper conductors and as a dielectric to insulate certain components for adjacent circuitry.

Photopolymerizable compositions containing the $\alpha,\beta$-unsaturated ketone sensitizers of this invention show good visible light sensitization. The increase in speed results in a saving of energy and costs related thereto since lower energy exposure sources can be used in exposure of the photopolymerizable element or more elements can be exposed and developed in a given amount of time. Alternatively, the photopolymerizable layer can be exposed by means of an exposure source maintained at a greater distance than normal for known sensitized elements. This permits the exposing radiation to be collimated which is of particular advantage in forming halftone dots having substantially perpendicular sides. The broad sensitization range coupled with the effectiveness of sensitization enables useful positive polymeric images to be formed by a double exposure process, first, imagewise in the ultraviolet region of the spectrum and then overall in the visible region of the spectrum utilizing specific nitroaromatic photoinhibitors.

The following Examples illustrate the invention, Examples 1, 4, 10 and 14 representing preferred embodiments. All parts and percentages are by weight and all degrees are Celsius unless otherwise stated. Examples 1 to 9 describe preparation of sensitizers and Examples 10 to 18 describe preparation of photopolymerizable compositions containing said sensitizers.

Preparation of Intermediates

The reactant, 1-(2,3-dihydro-1H-inden-5-yl)-ethanone (5), was prepared by the following procedure. To a 3-necked 1 liter round bottom flask equipped with a stirrer was added 60 g of indane and 50 g of acetyl chloride dissolved in 500 ml of methylene chloride. The reaction flask was cooled in an ice bath, and aluminum chloride (75 g) was added slowly through a piece of large rubber tubing. After the addition had been completed, the reaction mixture was heated under reflux for 2 hr with vigorous evolution of hydrogen chloride gas. The reaction mixture was cooled and poured into ice water which contained 50 ml of concentrated hydrochloric acid. The reaction mixture was extracted with ether and the ether extracts were combined and dried. The ether was evaporated and the residue distilled at 150° and water aspirator pressure to give 33.1 g (41%) of 1-(2,3-dihydro-1H-inden-5-yl)-ethanone. The reactant, 6-acetyl-1,2,3,4-tetrahydronaphthalene (1), is prepared from 1,2,3,4-tetrahydronaphthalene by a similar procedure.

The preparations of 3,5,6,7-tetrahydro-5-indacen-1(2H)-one (8, s-hydrindacen-1-one) and 2,3,5,6,7,8-hexahydro-1H-benz[f]inden-1-one (12) are described in detail by Dufour et al., J. C. S. Perkin I, p 527 to 530 (1972). Compound 8 was prepared as follows: Into a solution of hydrindene and β-chloropropionyl chloride in methylene chloride, powdered aluminum chloride was stirred during 1 hr at 18°; the solvent was then distilled off, the cooled residue was treated dropwise with sulphuric acid, and the mixture was heated. After decomposition with ice and extraction of the product in ether, the ketone was purified by distillation in vacuo and recrystallization from hexane.

Compound 12 was prepared by an alternate procedure as follows: Tetralin was formylated with dichloromethyl methyl ether and titanium tetrachloride catalyst to give 6-formyltetralin. Reaction of the aldehyde with malonic acid in the presence of an amine catalyst gave the substituted acrylic acid. Catalytic hydrogenation of the double bond gave the corresponding substituted propionic acid, 3-(6-tetralyl)propionic acid. Conversion of the acid to the acid chloride with phosphorus pentachloride followed by cyclization with aluminum chloride gave the desired 2,3,5,6,7,8-hexahydro-1H-benz[f]inden-1-one.

EXAMPLE 1

3-[4-(Dimethylamino)phenyl]-1-(5,6,7,8-tetrahydronaphthalen-2-yl)-2-propen-1-one (2)

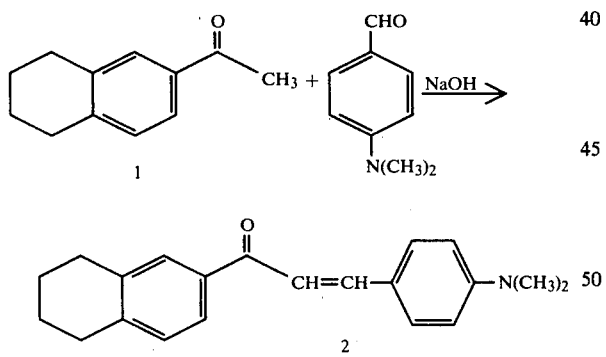

A solution of 2.61 g of 6-acetyl-1,2,3,4-tetrahydronaphthalene (15 mmoles) (1), 2.23 g of p-dimethylaminobenzaldehyde (15 mmoles), and 0.66 g of sodium hydroxide in 50 ml of ethanol was stirred under nitrogen at about 60° for 90 hr. The reaction mixture was cooled in an ice bath, and the precipitated solid 3-[4-(dimethylamino)phenyl]-1-(5,6,7,8-tetrahydroaphthalen-2-yl)-2-propen-1-one was collected by filtration and washed with cold ethanol. Yield: 3.0 g (61%); m.p. 134° to 135°. λmax (CHCl₃); 410 nm (ε=17,200); 266 nm (17,600). Calcd for $C_{21}C_{23}NO$: C, 82.59; H, 7.59; N, 4.59. Found: C, 80.38, 80.41; H, 7.30, 7.30; N, 3.59, 3.97.

EXAMPLE 2

3-[4-(1-Pyrrolidinyl)phenyl]-1-(5,6,7,8-tetrahydronaphthalen-2-yl)-2-propen-1-one (3)

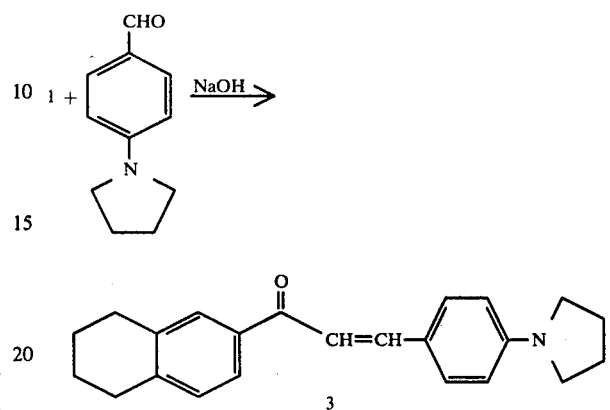

A solution of 2.6 g of 1 (15 mmol), 2.6 g of p-pyrrolidinylbenzaldehyde (15 mmol), and 0.66 g of sodium hydroxide in 100 ml of ethanol was stirred under nitrogen at 50° for 24 hr. The reaction mixture was cooled in an ice bath, and the precipitated yellow solid 3-[4-(1-pyrrolidinyl)phenyl]-1-(5,6,7,8-tetrahydronaphthalen-2-yl)-2-propen-1-one was collected by filtration and washed with cold ethanol. Yield: 3.2 g (64%); m.p. 167° to 169°. λmax (CHCl₃): 420 nm (ε=36,800); 330 nm (4,300); 276 nm (16,400). Calcd for $C_{23}H_{25}NO$: C, 83.34; H, 7.60; N, 4.23. Found: C, 82.68, 82.67; H, 7.57, 7.55; N, 4.03, 4.15.

EXAMPLE 3

3-[4-(4-Morpholinyl)phenyl]-1-(5,6,7,8-tetrahydronaphthalen-2-yl)-2-propen-1-one (4)

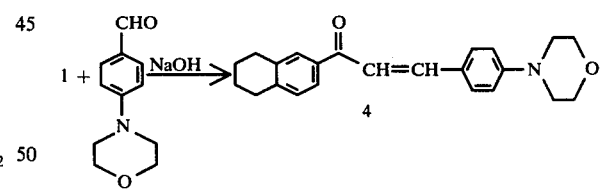

A solution of 1.74 g of 1 (10 mmoles), 1.91 g of p-(4-morpholinyl)benzaldehyde (10 mmoles), and two pellets of sodium hydroxide (about 0.4 g) in 40 ml of ethanol was stirred under nitrogen at room temperature for 70 hr. The reaction mixture was cooled in an ice bath and the precipitated yellow solid 3-[4-(4-morpholinyl)phenyl]-1-(5,6,7,8-tetrahydronaphthalen-2-yl)-2-propen-1-one was collected by filtration and washed with cold ethanol. Yield: 2.9 g (83%); m.p. 138° to 140°. λmax (EtOH): 390 nm (ε=28,100), 270 nm (ε=13,700). Calcd for $C_{23}H_{25}NO_2$: c, 79.51; H, 7.25; N, 4.03. Found: C, 78.72, 79.02, 78.75; H, 7.22, 7.26, 7.23; N, 3.88, 3.87, 3.91.

EXAMPLE 4

3-[4-(Dimethylamino)phenyl]-1-(2,3-dihydro-1H-inden-5-yl)-2-propen-1-one (6)

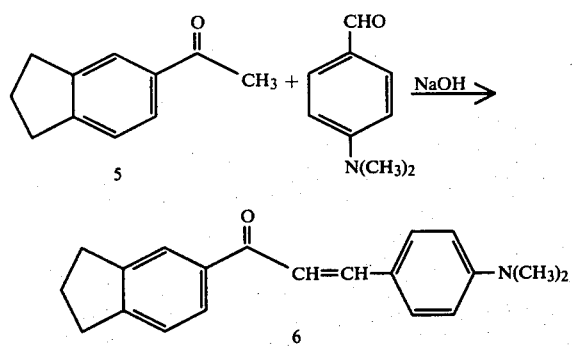

A solution of 4.8 g of 1-(2,3-dihydro-1H-inden-5-yl)ethanone 5; 30 mmoles), 4.5 g of p-dimethylaminobenzaldehyde (30 mmoles), and 1.32 g of sodium hydroxide in 40 ml of methanol was stirred under nitrogen at room temperature for 48 hr. The reaction mixture was cooled in an ice bath and the precipitated solid 3-[4-(dimethylamino)phenyl]-1-(2,3-dihydro-1H-inden-5-yl)-2-propen-1-one was collected by filtration and washed with cold methanol. Yield: 4.2 g (48%); m.p. 106° to 108°. λmax (EtOH): 416 nm (ε=34,700); 272 nm (15,400). Calcd for $C_{20}H_{21}NO$: C, 82.44; H, 7.26; N, 4.81. Found: C, 82.19, 82.12; H, 7.21, 7.24; N, 4.70, 4.67.

EXAMPLE 5

3-[4-(1-Pyrrolidinyl)phenyl]-1-(2,3-dihydro-1H-inden-5-yl)-2-propen-1-one (7)

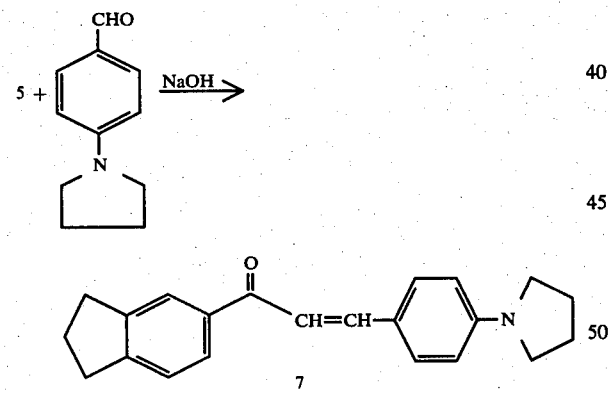

A solution of 1.47 g (9.14 mmoles) of 5, 1.60 g (9.14 mmoles) of p-pyrrolidinylbenzaldehyde and two pellets of sodium hydroxide (about 0.4 g) in 20 ml of methanol was stirred under nitrogen at room temperature for 112 hr. The reaction mixture was cooled in an ice bath and the precipitated solid 3-[4-(1-pyrrolidinyl)phenyl]-1-(2,3-dihydro-1H-inden-5-yl)-2-propen-1-one was filtered and washed with cold methanol. Yield: 1.2 g (41%); m.p. 162° to 164°. Evaporation of the filtrate gave a residue which was dissolved in methanol-toluene (9:1). The solution was filtered, evaporated to 100 ml, and cooled. The precipitated product was collected by filtration and washed with cold methanol. Yield: 0.9 g (31%); m.p. 177° to 179°. λmax (EtOH): 275 nm (ε=16,600); 328 nm (4170); 425 nm (37,800). Calcd for $C_{22}H_{23}NO$: C, 83.24; H, 7.30; N, 4.41. Found: C, 82.99; H, 7.49; N, 4.32.

EXAMPLE 6

2-[(4-(Dimethylamino)phenyl)methylene]-3,5,6,7-tetrahydro-5-indacen-1(2H)-one (9)

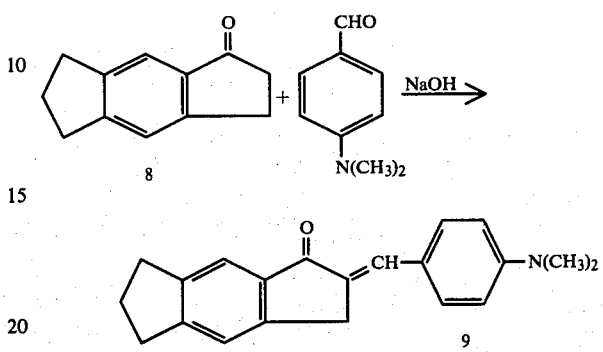

A solution of 2.06 g (12 mmoles) of 3,5,6,7-tetrahydro-5-indacen-1(2H)-one (8), 1.79 g (12 mmoles) of p-dimethylaminobenzaldehyde, and 0.59 g of sodium hydroxide in 40 ml of methanol was stirred under nitrogen at 50° for 24 hr. The reaction mixture was cooled in an ice bath and the precipitated solid 2-[(4-dimethylamino)phenyl)methylene]-3,5,6,7-tetrahydro-5-indacen-1(2H)-one was collected by filtration and washed with cold methanol. Yield: 3.2 g (88%); m.p. 210° to 225°. λmax (EtOH): 425 nm (ε=39,400); 325 nm (7,100); 273 nm (16,500). Calcd for $C_{21}H_{21}NO$: C, 83.13; H, 6.98; N, 4.62. Found: C, 83.27; H, 7.04; N, 4.53.

EXAMPLE 7

2-[(1,2,6,7-Tetrahydro-3H,5H-benzo[i,j]quinolizin-9-yl)methylene]-3,5,6,7-tetrahydro-5-indacen-1(2H)-one (10)

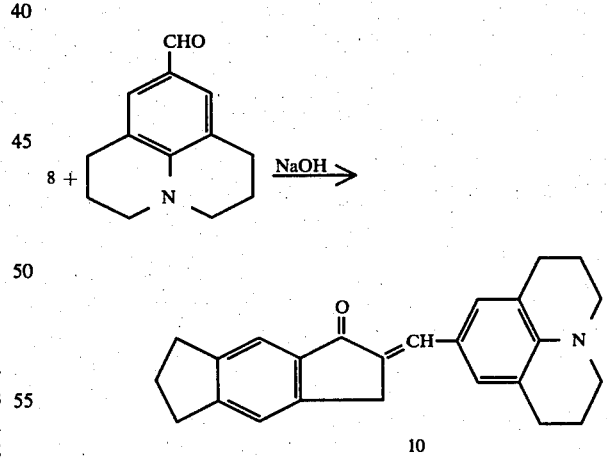

A solution of 2.06 g of 8, 2.41 g of 9-formyl-1,2,6,7-tetrahydro-3H,5H-benzo[i,j]-quinoline, and about 0.5 g of sodium hydroxide in 40 ml of methanol was stirred under nitrogen at 50° for 24 hr. The reaction mixture was cooled in an ice bath and the precipitated solid 2-[(1,2,6,7-tetrahydro-3H,5H-benzo[i,j]quinolizin-9-yl)methylene]-3,5,6,7-tetrahydro-5-indacen-1(2H)-one was filtered and washed with cold methanol. Yield: 3.2 g (75%); m.p. 186° to 189°. λmax (EtOH): 458 nm (ε=42,300); 285 nm (20,300). Calcd for $C_{25}H_{25}NO$: C, 84.47; H, 7.09; N, 3.94. Found: C, 83.68, 83.57; H, 7.09, 7.15; N, 3.85, 3.84.

EXAMPLE 8

2-[(1-Ethyl-1,2,3,4-tetrahydro-6-quinolinyl)-methylene]-3,5,6,7-tetrahydro-5-indacen-1(2H)-one (11)

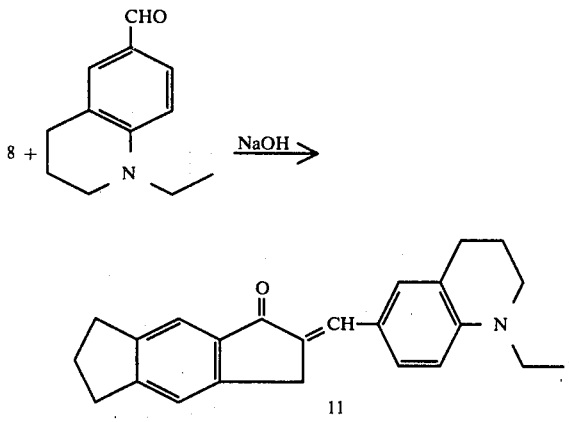

A solution of 1.72 g of 8, 1.89 g of 1-ethyl-6-formyl-1,2,3,4-tetrahydroquinoline and 0.44 g of sodium hydroxide in 25 ml of methanol was stirred under nitrogen at 60° for 48 hr. The reaction mixture was cooled in an ice bath and the precipitated solid 2-[(1-ethyl-1,2,3,4-tetrahydro-6-quinolinylmethylene-3,5,6,7-tetrahydro-5-indacen-1(2H)-one was collected by filtration and washed with cold methanol. Yield: 1.8 g (52%); m.p. 167° to 172°. λmax (EtOH): 282 nm ($\epsilon = 18,800$); 320 nm (7240); 332 nm (6280); 447 nm (43,300). Calcd for $C_{24}H_{25}NO$: C, 83.93; H, 7.34; N, 4.08. Found, C 83.45, 83.20, 83.10; H, 7.73; 7.33, 7.55; N, 3.94, 4.02, 4.01.

EXAMPLE 9

2-[(4-(Dimethylamino)phenyl)methylene]-2,3,5,6,7,8-hexahydro-1H-benz[f]inden-1-one (13)

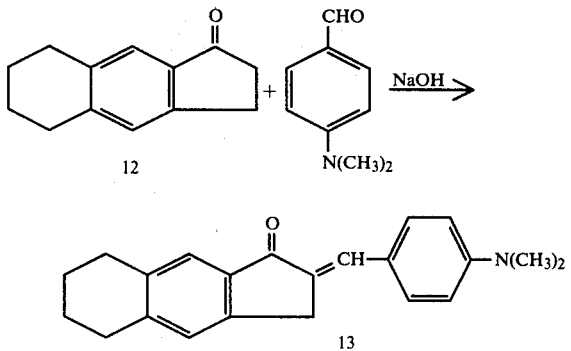

A solution of 1.84 g (10 mmoles) of 2,3,5,6,7,8-hexahydro-1H-benz[f]inden-1-one (12), 1.49 g (10 mmoles) of p-dimethylaminobenzaldehyde, and 0.44 g of sodium hydroxide in 25 ml ethanol was stirred under nitrogen at 50° to 60° for 19 hr. The reaction mixture was cooled in an ice bath and the precipitated solid 2-[4-(dimethylamino)phenyl)-methylene]-2,3,5,6,7,8-hexahydro-1H-benz[f]inden-1-one was collected by filtration and washed with cold ethanol. Yield: 2.5 g (79%); m.p. 161° to 163°. λmax (EtOH): 274 nm ($\epsilon = 16,700$); 422 nm (36,500). Calcd for $C_{22}H_{23}NO$: C, 83.24; H, 7.30; N, 4.41. Found: C, 83.01; H, 7.73; N, 4.34.

EXAMPLE 10

The oriented polyester films employed as substrates in Examples 10 to 18 were 4-mil (102 μm) polyethylene terephthalate films sub-coated with a copolymer resin. The copolymer resin comprised a sequentially polymerized mixture of a vinylidene chloride/alkyl acrylate/itaconic acid copolymer and an alkyl acrylate polymer as described in more detail in U.S. Pat. No. 3,443,950. To the copolymer resin, before coating, was added a methyl methacrylate: ethyl acrylate:acrylic acid (37:56:7) terpolymer (molecular weight 260,000 and acid number 76 to 85), dispersed with ammonia. The coated films were stretched and a thin layer of the terpolymer in water was added onto the first sub-coating.

| Component | Wt (g) |
|---|---|
| Tetraethylene glycol dimethacrylate | 15.0 |
| Terpolymer of ethyl acrylate/methyl methacrylate/acrylic acid (56/37/7), MW 260,000 | 35.3 |
| Copolymer of styrene/maleic anhydride (58/42), esterified, MW 10,000 | 36.7 |
| 2-(o-Chlorophenyl)-4,5-diphenyl-imidazolyl dimer | 8.6 |
| Methylene chloride | 527 |
| Methanol | 40. |

To 10 g of this stock solution was added 0.0407 g of 6-nitroveratraldehyde photoinhibitor and 0.0113 g of the sensitizer from Example 1. Portions of this solution were board coated with a 2-mil (51-μm) doctor knife on the resin-subbed side of the oriented polyester film substrate, and the coatings were air-dried. The dried coatings were laminated with a 1-mil (25-μm) oriented polyester film coversheet at 82° at a rate of 4 ft/min (1.22 m/min) at 40 psi (276 kPa).

One half the surface of a photosensitive element was covered by a black polyethylene sheet. A $^3\sqrt{2}$ step wedge process transparency was placed over the uncovered side and the element was placed in a vacuum printing frame. An imagewise exposure (positive exposure) was made to radiation from a 2 KW mercury photopolymer lamp at a distance of 38 in (96 cm) using an "Ascor" Light Integrator Platemaker Model 1415-12 with a Berkey "Ascor" 1601-40 light source for a time which corresponds to a radiation dosage of 10 units. The polyethylene sheet was removed and a $^3\sqrt{2}$ step wedge was placed over the previously blocked-off section.

A U.V. cut-off filter which absorbed essentially all radiation below about 420 nm was placed over the element and the entire element was given a 30 unit exposure. This final exposure gave a negative exposure to the blocked-off section and completed the two-exposure positive sequence on the other half. The exposed element was developed at 22° in a solution prepared from 1536 g of distilled water, 84 g of potassium carbonate.1.5 $H_2O$, and 5 g of potassium hydrogen carbonate, and the developed element was rinsed with a 32° water spray at 40 psi (276 kPa). A development time of 6 seconds gave a positive mode speed of 3, i.e., the first three steps of the positive image were unpolymerized, and a negative mode speed of 10, i.e., the negative image showed 10 full and partial polymerized steps.

EXAMPLES 11 AND 12

The photopolymerizable compositions of Examples 11 and 12 were prepared, exposed and developed as described in Example 10 except: (1) the sensitizers of Table 1 were employed and (2) development time of 7 seconds was used in Example 11. Positive mode speeds of 1 and <1 were obtained for Examples 11 and 12, respectively. Negative mode speeds were 11 and 16, respectively. A good image was obtained in each instance.

TABLE 1

| Example | Sensitizer of, g |
|---------|------------------|
| 11 | Example 2, 0.0123 |
| 12 | Example 9, 0.0117 |

EXAMPLES 13 TO 18

Photopolymerizable compositions were prepared, exposed, and developed as described in Example 10 with the following modifications. No 6-nitroveratraldehyde photoinhibitor was added to the compositions. The photosensitive elements were given one 10-unit negative exposure to the photopolymer lamp. A development time of 8 seconds was used. The results, summarized in Table 2, indicate that a good image was obtained in each instance.

TABLE 2

| Example | Sensitizer of, g | Photopolymerization Speed |
|---------|------------------|---------------------------|
| 13 | Example 3, 0.0129 | 11 |
| 14 | Example 4, 0.0108 | 12 |
| 15 | Example 5, 0.0117 | 12 |
| 16 | Example 6, 0.0112 | 12 |
| 17 | Example 7, 0.0132 | 12 |
| 18 | Example 8, 0.0127 | 12 |

I claim:

1. A photopolymerizable composition comprising the components:
   (i) at least one nongaseous ethylenically unsaturated compound capable of forming a high molecular weight polymer by photoinitiated addition polymerization;
   (ii) at least one 2,4,5-triarylimidazolyl dimer initiator consisting of two 2,4,5-triarylimidazolyl radicals bound together by a single covalent bond; and
   (iii) at least one $\alpha,\beta$-unsaturated ketone sensitizer having the formula

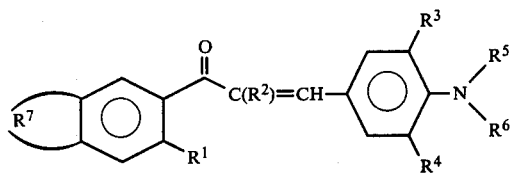

wherein
   $R^1$ and $R^2$ are each H, or $R^1+R^2$ is $-CH_2-$;
   $R^3$ is H, or $R^3+R^5$ is selected from $-CH_2-_2$, $-CH_2-_3$, and $-CH(CH_3)CH_2C(CH_3)_2-$;
   $R^4$ is H, or $R^4+R^6$ is selected from $-CH_2-_2$ and $-CH_2-_3$;
   $R^5$ and $R^6$ are alkyl groups of 1 to 5 carbon atoms, or together are selected from $-CH_2-_4$ and $-CH_2CH_2OCH_2CH_2-$;
   $R^7$, having a total of up to 8 carbon atoms, is selected from trimethylene and tetramethylene groups, unsubstituted, or substituted with 1 to 4 alkyl groups.

2. A photopolymerizable composition according to claim 1 wherein the components are present in these amounts, by weight:
   100 parts of (i),
   0.01 to 20 parts of (ii), and
   0.001 to 15 parts of (iii).

3. A photopolymerizable composition according to claim 2 containing 1 to 10 parts of (iii).

4. A photopolymerizable composition according to claim 1 comprising additionally a polymeric binder component, (iv).

5. A photopolymerizable composition according to claim 4 wherein the binder is selected from at least one member of the group polyacrylate esters and poly-$\alpha$-alkylacrylate esters containing carboxyl groups.

6. A photopolymerizable composition according to claim 4 wherein the components are present in these amounts, by weight:
   (i) is 3 to 100 parts per 100 parts of (i) plus binder,
   (ii) is 0.01 to 20 parts per 100 parts of (i) plus binder,
   (iii) is 0.001 to 15 parts per 100 parts of (i) plus binder, and
   (iv) is 0 to 97 parts per 100 parts of (i) plus binder.

7. A photopolymerizable composition according to claim 6 wherein (iii) is 1 to 10 parts per 100 parts of (i) plus binder.

8. A photopolymer of the composition according to claim 1.

9. A photopolymer of the composition according to claim 4.

* * * * *